United States Patent [19]

Nishihira et al.

[11] Patent Number: 5,315,032
[45] Date of Patent: May 24, 1994

[54] METHOD OF PRODUCING AN N-HYDROXYCARBAMATE COMPOUND

[75] Inventors: Keigo Nishihira; Shuji Tanaka; Katsuhiko Mizutare; Masahiro Kondo, all of Ube, Japan

[73] Assignee: Ube Industries, Ltd., Yamaguchi, Japan

[21] Appl. No.: 67,551

[22] Filed: May 26, 1993

[30] Foreign Application Priority Data

May 26, 1992 [JP] Japan ................... 4-189803
Nov. 26, 1992 [JP] Japan ................... 4-317125

[51] Int. Cl.$^5$ ........................................... C07C 261/00
[52] U.S. Cl. .................................. 560/157; 560/137
[58] Field of Search ............................ 560/157, 137

[56] References Cited

U.S. PATENT DOCUMENTS 4,160,077  7/1979  Brooks ..................... 560/157

FOREIGN PATENT DOCUMENTS 3245503  6/1984  Fed. Rep. of Germany .

OTHER PUBLICATIONS

Drug Preparations & Procedures Int'l, vol. 19, No. 1, pp. 75-78 Authors: O. P. Goel and U. Krolls 1987.

*Primary Examiner*—Michael L. Shippen
*Attorney, Agent, or Firm*—Burgess, Ryan and Wayne

[57] ABSTRACT

An N-hydroxycarbamate compound of the formula ROCONHOH in which R is $C_{1-8}$ alkyl, $C_{3-12}$ cycloalkyl, aryl or aralkyl group, is produced by reacting a carbonic acid diester of the formula ROCOOR in which R is as defined above, with hydroxylamine in the presence of a basic substance, for example, an alkali metal hydroxide or alkoxide.

11 Claims, No Drawings

METHOD OF PRODUCING AN N-HYDROXYCARBAMATE COMPOUND

BACKGROUND OF THE INVENTION

1. Field of the Invention

The present invention relates to a method of producing an N-hydroxycarbamate compound. The N-hydroxycarbamate compound is useful as a raw material for synthesizing medicines and pesticides.

2. Description of Related Art

As a conventional synthesizing method for an N-hydroxycarbamate compound, it is known to react hydroxylamine with a chloroformic acid ester. For example, German Patent No. 3,245,503 discloses a method of synthesizing (N-hydroxy) butyl carbamate by reacting hydroxylamine with butyl chloroformate.

Also, Org. Prep. and Procedures International, 19(1), 75(1987) discloses a method of synthesizing (N-methoxy-N-methyl)ethylcarbamate by preparing (N-hydroxy)ethylcarbamate from ethyl chloroformate and hydroxylamine hydrochloride and then methylating (N-hydroxy)ethylcarbamate with a methylating agent, in accordance with the reactions [A] and [B]:

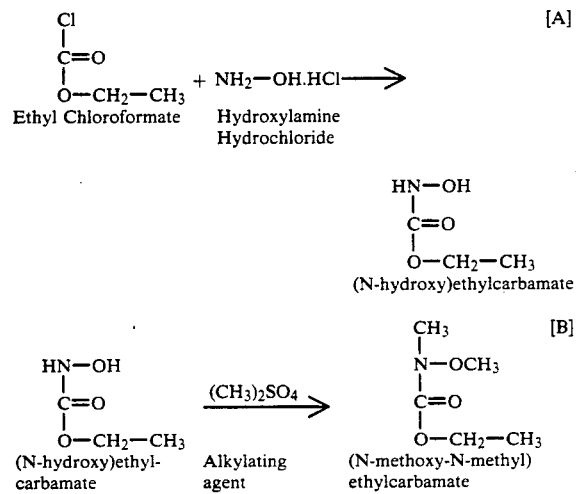

As the above-mentioned reference discloses, (N-methoxy-N-methyl)ethylcarbamate can be converted to an alkoxyalkylamine by a hydrolysis and decarboxylation reaction procedure in which (N-methoxy-N-methyl)ethylcarbamate is mixed with an acid and the mixture is heated. The alkoxyalkylamine is useful as an intermediate for pesticides. The preparation of the alkoxyalkylamine is carried out in accordance with the reaction [C]:

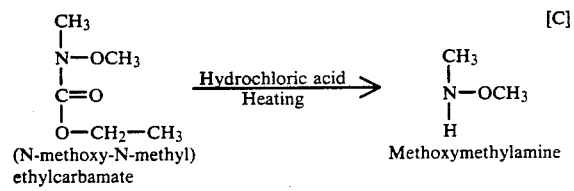

Nevertheless, the above-mentioned prior art method is disadvantageous in that the chloroformic acid ester used in this method is usually produced from phosgene, which is a strong toxicant, and ethyl alcohol in accordance with the reaction [D]:

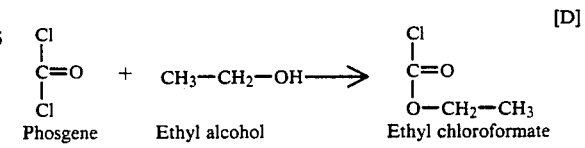

Accordingly, a new method in which no strongly toxic phosgene is used is demanded to provide the N-hydroxycarbamate.

Also, the chloroformic acid ester per se has a strong toxicity and corrosiveness and thus must be carefully handled, and reacted in a specific reactor having a high resistance to corrosion, and is expensive as an industrial material.

Therefore, the conventional method of producing N-hydroxycarbamate is not satisfactory for industrial utilization.

SUMMARY OF THE INVENTION

As mentioned above, the conventional method of producing an N-hydroxycarbamate compound is disadvantageous in that in this method, a chloroformic acid ester, which is expensive and strongly toxic and corrosive, must be employed as a reactant.

An object of the present invention is to provide a new method of producing an N-hydroxycarbamate compound by using materials which are cheap and can be easily handled.

The inventors of the present invention investigated a new method of producing an N-hydroxycarbamate compound, by which method the above-mentioned disadvantages of the conventional methods are eliminated, and consequently discovered that the N-hydroxycarbamate compound can be produced by simple procedures with a high yield by using a carbonic acid diester compound as a starting material. The present invention was completed on the basis of this discovery.

The method of the present invention for producing an N-hydroxycarbamate compound of the formula (I):

wherein R represents a member selected from the group consisting of alkyl groups having 1 to 8 carbon atoms, cycloalkyl groups having 3 to 12 carbon atoms, aryl groups and aralkyl groups, comprises reacting a carbonic acid diester compound of the formula (II):

wherein R is as defined above, with hydroxylamine in the presence of a basic substance.

DESCRIPTION OF THE PREFERRED EMBODIMENTS

The production of an N-hydroxycarbamate compound of the formula (I) in accordance with the method of the present invention is carried out by reacting a carbonic acid diester compound of the formula (II) with hydroxylamine (which may be a hydrochloric acid salt or sulfuric acid salt thereof) in the presence of a basic substance. Namely, the N-hydroxycarbamate compound is produced in accordance with the reaction formula [E]:

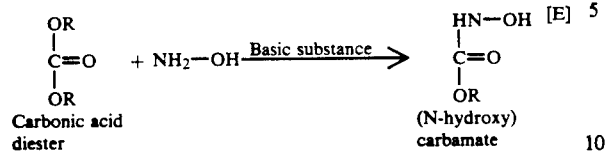

Carbonic acid diester (N-hydroxy) carbamate

In the carbonic acid diester compound of the formula (II), ROCOOR in which R represents a member selected from the group consisting of alkyl groups having 1 to 8 carbon atoms, cycloalkyl groups having 3 to 12 carbon atoms, aryl groups and aralkyl groups, which compound is used as a starting material for the method of the present invention, the hydrocarbon group represented by R is the same as the group represented by R in the formula (I) for the intended N-hydroxycarbamate compound.

In the formulae (I) and (II), the group R is selected from straight chain or branched chain alkyl groups having 1 to 8 carbon atoms, for example, methyl, ethyl, n-propyl, isopropyl, n-butyl, isobutyl, tert-butyl, and hexyl groups; cycloalkyl group having 3 to 12 carbon atoms, for example, cyclopropyl cyclohexyl and cyclododecyl groups; aryl groups, for example, phenyl group; and aralkyl groups, for example, benzyl group.

The carbonic acid diester of the formula (II) is preferably selected from the group consisting of dimethyl carbonate, diethyl carbonate, di-n-propyl carbonate, di-isopropyl carbonate, di-n-butyl carbonate, di-isobutyl carbonate, di-tert-butyl carbonate, dihexyl carbonate, dicyclohexyl carbonate, dicyclododecyl carbonate, diphenyl carbonate and dibenzyl carbonate.

Hydroxylamine, which is another starting material for the method of the present invention, may be in the form of a free base or in the form of an inorganic acid salt, for example, a hydrochloric acid salt or a sulfuric acid salt thereof. Usually, hydroxylamine is used in the state of a solution thereof in water.

In the method of the present invention, the reaction in accordance with the formula [E] is carried out in the presence of a basic substance while effectively controlling and adjusting the pH of the reaction solution to a desired level during the reaction procedure.

The basic substance preferably comprises at least one member selected from the groups consisting of powdery hydroxides of alkali metals and of alkaline earth metals, for example, sodium hydroxide, potassium hydroxide and calcium hydroxide, and alkoxides of alkali metals, for example, sodium methoxide, sodium ethoxide and potassium methoxide. Preferably, the basic substance, for example, the hydroxides of alkali metals or alkaline earth metals are added in the form of a solution in water or in an alcohol to the reaction solution.

In the method of the present invention, it is important to adjust the reaction rate to a desired level by controlling the pH of the reaction solution within an adequate range. Preferably, the pH of the reaction solution is controlled to 7 or more, more preferably 10 to 13.

In the method of the present invention, when the reaction medium contains water in a small amount, and an alkoxide is used as a basic substance for controlling the pH of the reaction solution, the control of pH is difficult. In this case, the reaction solution is preferably added with an alkoxide in an amount of 0 to 2 moles per mole of hydroxylamine contained in the reaction solution. Where hydroxylamine hydrochloric acid salt is used, the alkoxide is preferably used in an amount of 1 to 3 moles per mole of the hydroxylamine hydrochloric acid salt. Also, where hydroxylamine sulfuric acid salt is used, the alkoxide is preferably employed in an amount of 2 to 6 moles per mole of the hydroxylamine sulfuric acid salt. More preferably, the alkoxide is employed in an amount of 0.5 to 1 mole per mole of hydroxylamine, or 1.5 to 2 moles per mole of hydroxylamine hydrochloric acid salt or 3 to 4 moles per mole of hydroxylamine sulfuric acid salt.

In the method of the present invention, it is characteristic that the reaction of the carbonic acid diester with hydroxylamine in accordance with the reaction formula [E] can be effected under moderate reaction conditions. For example, the reaction can be carried out under any pressure in wide range from reduced pressure to enhanced pressure. Namely, there is no limitation on the reaction pressure. Practically, the reaction is carried out preferably under a pressure of from 500 torr to 5 kg/cm²G, more preferably from ambient atmospheric pressure to 2 kg/cm²G for industrial practice.

Also, the reaction can be carried out at a moderate temperature of from −20° C. to 100° C. Preferably, the reaction temperature is in the range of from 0° C. to 60° C. in which undesirable side reactions can be prevented. When the reaction temperature is controlled in the above-mentioned range, the reaction can be carried out at a satisfactory reaction rate.

In the reaction of carbonic acid diester with hydroxylamine in accordance with the reaction formula [E], a reaction medium (solvent) is not always necessary. Nevertheless, the reaction medium is optionally employed to make the reaction procedure easy. In this case, there is no restriction to the type of the reaction medium as long as it is inert to the carbonic acid diester and hydroxylamine to be used as reactants and to the reaction product, namely N-hydroxycarbamate.

The reaction medium usable for the method of the present invention comprises at least one solvent selected from the group consisting of, for example, water; aliphatic alcohols, for example, methyl alcohol, ethyl alcohol, n-propyl alcohol, isopropyl alcohol, n-butyl alcohol and isobutyl alcohol; aromatic hydrocarbons, for example, benzene, toluene and xylene; aliphatic and cycloaliphatic hydrocarbons, for example, n-hexane, n-heptane, and cyclohexane; ethers, for example, diisopropylether, tetrahydrofuran, and ethyleneglycoldimethyl-ether; and nitriles, for example, acetonitrile, propionitrile and benzonitrile.

Where the above-mentioned aliphatic alcohol is used as a reaction medium, preferably the alcohol is selected from those capable of forming the same ester group as the ester group in the carbonic acid ester used for the method of the present invention. When the above-mentioned type of alcohol is used, undesirable transesterification reaction of the carbonic acid ester is substantially avoided.

When the reaction medium is used, there is no restriction on the amount thereof. However, if the amount of the reaction medium is too small, a resultant slurry of the N-hydroxycarbamate compound is too thick and exhibits a poor handling property. If the amount of the reaction medium used is too large, the cost for recovering the reaction medium becomes too high. Therefore, the reaction medium is preferably used in an amount of 1 to 20 parts by weight, more preferably 1 to 3 parts by weight per part by weight of the carbonic acid diester compound.

With respect to the proportions of the reactants to be used in the reaction system, if the carbonic acid diester is used in an excessive amount, the resultant N-hydroxy carbamate compound reacts with the remaining portion of the carbonic acid diester and thus the yield of the N-hydroxycarbamate compound is reduced. Also, if hydroxylamine is employed in an excessive amount, although there is no problem in the reaction per se, the recovery of non-reacted hydroxylamine is difficult, and thus the non-reacted hydroxylamine may be wasted. This increases the cost of the reaction. Accordingly, hydroxylamine is preferably used in an amount of 0.5 to 2 molar parts, more preferably 0.9 to 1.2 molar parts per molar part of the carbonic acid diester compound.

Where the reaction of the carbonic acid diester compound with hydroxylamine is carried out in a reaction medium, and the resultant reaction mixture contains an inorganic salt, for example, sodium chloride or sodium sulfate, the inorganic salt is removed from the reaction mixture by filtration, the reaction medium is recovered from the filtrate, and then the resultant N-hydroxycarbamate compound is isolated in a high degree of purity by distillation or crystallization.

The N-hydroxycarbamate compound obtained by the method of the present invention can be converted to an (N-alkoxy-N-alkyl) carbamate compound, for example, (N-methoxy-N-methyl) methylcarbamate, by alkylating the N-hydroxycarbamate compound with an alkylating agent, for example, a methylating agent such as dimethylsulfuric acid.

Further, the (N-alkoxy-N-alkyl) carbamate compound can be used to synthesize an alkoxyalkylamine compound which is usable as an intermediate for useful compounds, for example, pesticides, by hydrolysis and decarboxylation by an appropriate method in accordance with the known reaction (C).

In the process for producing the above-mentioned (N-alkoxy-N-alkyl) carbamate compound, a concentrated reaction liquid (aqueous solution or a solution in alcohol) containing the N-hydroxycarbamate compound produced by the method of the present invention is diluted with water or an alcohol (for example, methyl alcohol or ethyl alcohol) to an appropriate concentration, the concentration-controlled reaction liquid is added with an alkylating agent, for example, methylating agent such as dimethylsulfuric acid, and the resultant mixture is subjected to a reaction for 2 to 10 hours, while maintaining the temperature of the reaction mixture at a constant level of from 0° C. to 20° C. by cooling and while maintaining the pH of the reaction mixture in the range of from 12 to 12.5 by gradually adding a basic compound (for example, sodium hydroxide or alkyl alcoholate.

In this reaction procedure, the alkylating agent such as dimethylsulfuric acid is used in an amount of 0.5 to 3 molar parts, preferably 0.8 to 1.5 molar parts per molar part of the N-hydroxycarbamate compound.

When the reaction is completed, the reaction product is extracted from the reaction mixture by using an organic solvent, for example, toluene, methylene chloride or chlorobenzene, and then the extracted solution is concentrated by evaporating the organic solvent from the extracted solution, or the extracted solution is subjected to a distillation, to isolate the resultant (N-alkoxy-N-alkyl) carbamate compound.

The resultant (N-alkoxy-N-alkyl) carbamate compound (or its solution) is mixed with an aqueous solution of acid compound of, for example, hydrochloric acid (in a concentration of 10 to 40% by weight, preferably 20 to 35% by weight), the resultant reaction mixture is heated at a temperature of 40° C. to 100° C., preferably 65° C. to 90° C. for 1 to 30 hours, preferably 5 to 15 hours, to prepare, for example, a hydrochloric acid salt of alkoxyalkylamine compound by hydrolyzing and decarboxylating the (N-alkoxy-N-alkyl) carbamate compound.

In the hydrolysis and decarboxylation reaction, the hydrochloric acid is used in an amount of 1.1 to 3 molar parts, preferably 1.4 to 2.0 molar parts per molar part of the (N-alkoxy-N-alkyl) carbamate compound.

In accordance with the method of the present invention, the N-hydroxycarbamate compound, which is useful as an intermediate for various useful chemical compounds, can be industrially produced from a carbonic acid diester and hydroxylamine, which are not toxic and can be easily handled, with a high yield, without employing a chloroformic acid ester and phosgene, which are highly toxic and corrosive and used in the conventional method of producing same.

EXAMPLES

The present invention will be further explained by the following specific examples. Those examples are in no way intended to restrict the scope of the present invention.

EXAMPLE 1

A four-necked flask equipped with a thermometer, a dropping funnel, a pH meter and a stirrer and having a capacity of 500 ml was charged with 41 g (0.25 mole) of hydroxylamine sulfuric acid salt (corresponding to 0.50 mole of hydroxylamine), dissolved in 100 ml of water, and then with 54 g (0.60 mole) of dimethyl carbonate. The resultant reaction liquid was cooled to a temperature of 10° C., and then mixed with a 20% aqueous solution of sodium hydroxide over a period of 30 minutes to adjust the pH of the reaction liquid to a level of 12.0. The amount of the added aqueous sodium hydroxide solution was 168 g (0.84 mole).

The reaction liquid was maintained at a temperature of 20° C. for 5 hours while stirring to cause dimethyl carbonate to react with hydroxylamine.

After the reaction was completed, the resultant reaction liquid was subjected to a gas chromatographic analysis to determine the amount of the resultant reaction product. It was confirmed that (N-hydroxy) methylcarbamate was obtained in an amount of 43.0 g (0.47 mole) and in an yield of 95% based on the molar amount of hydroxylamine used.

EXAMPLE 2

A three-necked flask equipped with a thermometer, a dropping funnel and a stirrer and having a capacity of 500 ml was charged with 35 g (0.50 mole) of hydroxylamine sulfuric acid salt, then 100 ml of methyl alcohol, and finally 45 g (0.50 mole) of dimethyl carbonate.

The resultant mixture was gradually mixed with 162 g of a 28% aqueous solution of sodium methoxide (0.84 mole) at a temperature of 20° C. over a period of 30 minutes, and then the resultant reaction liquid was subjected to reaction at a temperature of 20° C. while stirring.

After the reaction was completed, the resultant reaction liquid was subjected to a gas chromatographic analysis to determine the amount of the reaction product. It was confirmed that (N-hydroxy) methyl carbamate was obtained in an amount of 40.1g (0.44 mole) corresponding to an yield of 88% based on the molar amount of hydroxylamine used.

EXAMPLE 3

A four-necked flask equipped with a thermometer, a dropping funnel, a pH meter and a stirrer and having a capacity of 500 ml was charged with 35 g (0.50 mole) of hydroxylamine sulfuric acid salt, then 100 ml of methyl alcohol to provide a solution of hydroxylamine sulfuric acid salt by stirring. The solution was mixed with 45 g (0.50 mole) of dimethyl carbonate, and the resultant mixture was cooled to a temperature of 10° C. The mixture was mixed dropwise with 162 g of an aqueous 28% solution of sodium methoxide (0.84 mole) at a temperature of 10° C. over a period of 20 minutes and then the resultant reaction liquid was subjected to reaction at a temperature of 10° C. for 3 hours while stirring.

After the reaction was completed, sodium chloride produced by the reaction was removed by filtration, and the filtrate was concentrated under a reduced pressure of 200 torr by removing methyl alcohol.

The concentrated filtrate was subjected to a gas chromatographic analysis. It was confirmed that (N-hydroxy) methylcarbamate was obtained at an amount of 41 g (0.45 mole).

REFERENTIAL EXAMPLE 1

Preparation of (N-methoxy-N-methyl) Methyl Carbamate

The same four-necked flask as used in Example 3 was further equipped with a pH meter, and then the concentrated liquid prepared in Example 3 containing 41 g of (N-hydroxy) methylcarbamate was mixed with 100 ml of water. Dimethyl sulfate and an aqueous 48 weight % sodium hydroxide solution were simultaneously added dropwise to the above-mentioned mixture, while stirring. During this operation, the temperature of the resultant reaction liquid was maintained in the range of from 10° C. to 20° C. and the pH of the reaction liquid was adjusted to a level of about 12 by controlling the dropping rate of the aqueous sodium hydroxide solution. In the above-mentioned reaction procedure, the total amount of the dropped dimethyl sulfate was 126 g (1.00 mole), and after the completion of the dropping operation, the reaction was further continued for 3 hours, while stirring.

After the reaction was completed, the resultant reaction liquid was subjected to a gas chromatographic quantitative analysis. It was confirmed that the reaction liquid contained (N-methoxy-N-methyl) methylcarbamate in an amount of 48 g (0.40 mole).

The reaction liquid was diluted with an extraction medium consisting of 100 ml of methylene chloride to extract 46 g of (N-methoxy-N-methyl) methylcarbamate in a methylene chloride phase. Then methylene chloride was evaporated from the extracted solution under a reduced pressure of 100 torr, to concentrate the extracted solution.

A portion of the concentrated solution was withdrawn therefrom, and methylene chloride was evaporated away to isolate the reaction product. The isolated product was subjected to a chemical structure-identification analysis. The results are shown in Table 1.

TABLE 1

| Analysis item | | Measurement result |
| --- | --- | --- |
| $^1$H-NMR(CDCl$_3$, TMS, ppm) | | 3.14 (3H, s, N—CH) |
| | | 3.70 (3H, s, N—OCH$_3$) |
| | | 3.77 (3H, s, C—OCH$_3$) |
| IR (CCl$_4$, cm$^{-1}$) | | 2957 ($\nu_{as}$ CH$_3$) |
| | | 1713 ($\nu$ C=O) |
| | | 1445 ($\delta_{as}$ CH$_3$) |
| | | 1356 ($\delta_s$ CH$_3$) |
| MS (M/z) | | 119 (M+) |
| Physical property | m.p | −28.5° C. |
| | b.p | 60° C./30 torr |

REFERENTIAL EXAMPLE 2

To the concentrated solution of (N-methoxy-N-methyl) methylcarbamate produced by the same procedures as in Referential Example 1, 58 g of an aqueous solution of 36% by weight of hydrochloric acid (0.57 mole) was added. The reaction mixture was stirred at a temperature of 75° C. for 6 hours to hydrolyze and decarboxylate (N-methoxy-N-methyl) methylcarbamate.

The resultant reaction mixture was subjected to a gas chromatographic analysis. It was confirmed that no (N-methoxy-N-methyl) methylcarbamate remained in the resultant reaction mixture.

The reaction mixture was concentrated under a reduced pressure, and mixed with n-butyl alcohol. The mixture was cooled to allow a reaction product to crystallize and precipitate from the mixture. Methylmethoxyamine hydrochloric acid salt was obtained in an amount of 35 g (0.36 mole).

What is claimed is:

1. A method of producing an N-hydroxycarbamate compound of the formula (I):

wherein R represents a member selected from the group consisting of alkyl groups having 1 to 8 carbon atoms, cycloalkyl groups having 3 to 12 carbon atoms, aryl groups and aralkyl groups,
comprising reacting a carbonic acid diester of the formula (II):

wherein R is as defined above, with hydroxylamine in the presence of a basic substance.

2. The method as claimed in claim 1, wherein, the carbonic acid diester of the formula (II) is selected from the group consisting of dimethyl carbonate, diethyl carbonate, di-n-propyl carbonate, di-isopropyl carbonate, di-n-butyl carbonate, di-isobutyl carbonate, di-tert-butyl carbonate, dihexyl carbonate, dicyclohexyl carbonate, dicyclododecyl carbonate, diphenyl carbonate and dibenzyl carbonate.

3. The method as claimed in claim 1, wherein the hydroxylamine is in the form of an inorganic acid salt.

4. The method as claimed in claim 1, wherein the basic substance comprises at least one member selected from the group consisting of hydroxides of alkali metals, hydroxides of alkaline earth metals and alkoxides of alkali metals.

5. The method as claimed in claim 1, wherein the reaction is carried out at a pH of 7.0 or more.

6. The method as claimed in claim 1, wherein the reaction is carried out under a pressure of 500 torr to 5 kg/cm²G

7. The method as claimed in claim 1, wherein the reaction is carried out at a temperature of $-20°$ C. to 100° C.

8. The method as claimed in claim 1, wherein the reaction is carried out in an inert reaction medium.

9. The method as claimed in claim 8, wherein the reaction medium comprises at least one member selected from the group consisting of water, aliphatic alcohols, aromatic hydrocarbons, aliphatic hydrocarbons, cycloaliphatic hydrocarbons, aliphatic ethers and nitrile compounds.

10. The method as claimed in claim 8, wherein the reaction medium is present in an amount of 1 to 20 parts by weight per part by weight of the carbonic acid diester.

11. The method as claimed in claim 1, wherein the hydroxylamine is present in an amount of 0.5 to 2 molar parts per molar part of the carbonic acid ester.

* * * * *